United States Patent [19]

Sagi et al.

[11] Patent Number: 4,536,433
[45] Date of Patent: Aug. 20, 1985

[54] SLIP RESISTANT ABSORBENT PAD

[76] Inventors: Zsigmond L. Sagi, 25 Arden Rd., Denville; Craig R. Hof, 112 Santa Fe Trail, Hopatcong, both of N.J. 07834

[21] Appl. No.: 532,796

[22] Filed: Sep. 16, 1983

[51] Int. Cl.³ .................... B32B 27/06; B32B 3/10
[52] U.S. Cl. ................................. 428/195; 428/484; 604/358
[58] Field of Search ............... 428/172, 195, 484, 487; 604/378, 385, 358

[56] References Cited

U.S. PATENT DOCUMENTS

| | | | |
|---|---|---|---|
| 2,224,189 | 10/1940 | Leslie | 428/195 |
| 3,400,008 | 9/1968 | Bleyle et al. | 428/484 |
| 3,681,117 | 8/1972 | Jolly et al. | 428/484 |
| 4,173,046 | 11/1979 | Gallagher | 604/378 |

Primary Examiner—Paul J. Thibodeau

[57] ABSTRACT

A slip resistant article such as an underpad comprises a moisture-absorbent layer and a water-impervious layer. One surface of the water-impervious layer is in contact with a mattress seat of a wheelchair and the like articles, and is treated with a material which has a high coefficient of friction to prevent the pad from slipping or sliding out of position relative to the surface of such articles when the patient moves about.

4 Claims, 3 Drawing Figures

SLIP RESISTANT ABSORBENT PAD

FIELD OF THE INVENTION

This invention relates generally to slip resistant articles (e.g., underpads and disposable diapers) and is particularly related to such articles which are especially treated to prevent thier slippage relative to the underlying surface on which they are placed.

BACKGROUND OF THE INVENTION

It is a matter of common knowledge that absorbent underpads are usually provided with a moisture-impervious underlayer to prevent patients' excrements or fluids from wetting or soiling the mattress or the fabric upon which the pad is placed, typically, a plastic sheet such as polyethylene or polypropylene. For example, Polygard II, a trademark for underpads sold by Professional Medical Products, Greenwood, N.C., consists of an absorbent pulp layer covered with a moisture-permeable non-woven fabric on one side, and a polypropylene film on the opposite side.

In a typical use, the underpad is placed on top of a patient's bedding with the polypropylene film facing against the bedding. Thus, the absorbent layer serves to absorb the patient's excrements or fluid while the polypropylene film prevents these excrements or fluids from passing through and soiling the bedding material. Such underpads are also used for placing on seats, such as on wheelchair seats, and on examination tables and the like article, and serve a similar function.

One of the difficulties of using such plastic films is that they have low coefficient of friction and, therefore, the underpads tend to slip and slide out of position when the patient moves about in bed or in the seat. Consequently, they fail to protect the bedding or seat underlying surfaces from being soiled.

One solution to this problem is to interpose several such protective underlayers so that at least one or more layer is always covering the mattress. This, however, is an inconvenient solution and furthermore, it is uneconomical.

Accordingly, it is an object of this invention to provide a non-slip or slip-resistant article such as underpads, disposable diapers and the like.

It is another object of this invention to provide such articles which are especially treated to provide a surface having a high friction coefficient which prevents the article from slipping or sliding relative to the surface upon which it is placed.

It is still another object of this invention to provide non-slipping underpads which serve to prevent patients' excrements or fluids from passing therethrough, and hence it serves to protect the underlying articles being soiled.

The foregoing and other features and advantages of the present invention will become more evident from the following detailed description and the accompanying drawings.

SUMMARY OF THE INVENTION

In accordance with this invention, there is provided a non-slip article (e.g., underpad) having a surface treated to exhibit high coefficient of friction. The underpad comprises a moisture-absorbent layer and a water-impervious sheet superimposed thereon. The surface of the water-impervious sheet which is normally in contact with the underlying article is treated with a material having high coefficient of friction in order to prevent the pad from slipping or sliding out of position when the patient moves about in the bed.

Certain waxes to be hereinafter defined are employed to treat the surface of the water-impervious sheet in order to impart high coefficient of friction thereto.

Also, this invention contemplates disposable articles having a moisture-impervious layer which is treated with a material having high coefficient of friction to prevent slippage or sliding relative to the underlying surfaces.

DETAILED DESCRIPTION OF THE INVENTION

It has been surprisingly discovered that when the outer surface of the pad's protective layer is coated with certain waxes, slippage of the pad relative to the underlying surface can be substantially eliminated. Thus, by applying such waxes to the outer surface of the plastic sheet, the sheet's surface will have a high coefficient of friction relative to the underlying surface and hence, when the patient moves about in the bed, the pad does not slip or slide out of position, thus protecting the underlying article from the patient's excrements or fluids.

The waxes which are suitable for the purpose of this invention must have certain properties which will not only impart high coefficient of friction to the plastic outer surface but which resist blocking when several pads are used or piled on top of each other such as during storage or even in use in the same bed. Thus, in general, the wax must have sufficiently high needle penetration value (as determined by ASTM D-1321) so as to impart the desired degree of slip resistance when applied to the surface of the underpad, and its melting point (as determined by ASTM D-127) must be high enough so as to resist blocking. Thus the needle penetration value of the wax must be from about 5 to about 70 while its melting point can vary from about 150° F. to about 200° F.

Multiwax ML 445, available from the Sonneborne Division of Witco Chemicals, has been found to be particularly effective in imparting high coefficient of friction to the plastic's outer surface without blocking or any other adverse effects. This wax has a needle penetration point of 30 at 77° F. and a melting point of 173° F. as determined by ASTM D-1321 and ASTM D-127, respectively.

The wax can be applied to the plastic's outer surface by various methods. In one method, the wax is dissolved in a suitable solvent such as heptane, at elevated temperatures, and then cooled to form a dispersion. The dispersion is then applied to form a coating on the outer plastic surface, or it may be applied thereto locally to form one or more areas of high coefficient of friction. In another and preferred method the wax is applied from a wax melt.

As it was previously mentioned, the wax coating may be continuous or it may be applied in different patterns.

Suffice it to say that when the wax is not applied as a continuous coating, there must be sufficient areas of the plastic surface coated with the wax to provide the desired degree of slip-resistance between the pad and the mattress.

Figure 1:
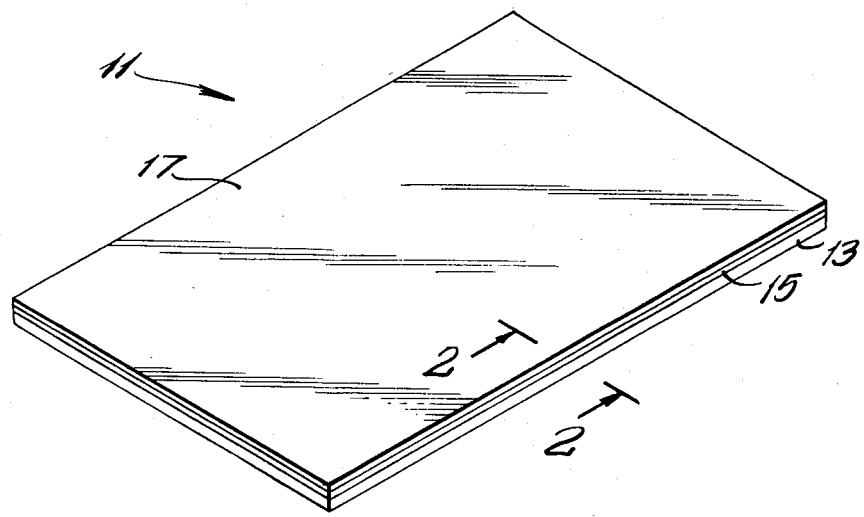
FIG. 1 is a perspective view of an underpad incorporating the present invention.
Figure 2:
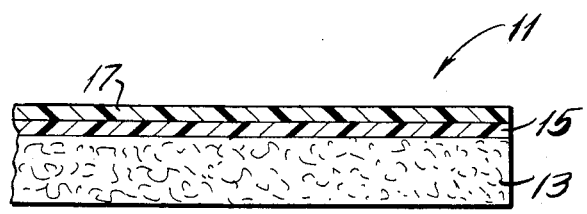
FIG. 2 is a sectional view taken along the line 2—2 of FIG. 1 illustrating the invention.

Referring now to the drawings, a typical pad designated as 11 is shown in perspective view in FIG. 1. As shown in FIG. 2, the pad 11 comprises a moisture-absorbent layer 13 made of fabric, plastic or other conventional material well known to those skilled in the art. While FIG. 2 is not drawn to scale, nevertheless the moisture-absorbent layer 13 is usually considerably thicker than the other layers to provide adequate comfort and support. The moisture-absorbent layer 13 is covered with a plastic sheet or layer 15 which may be superimposed on the layer 13 to provide a moisture barrier. The layer 15 is made of water-impervious plastic which is typically polyethylene or polypropylene. In the embodiment shown in FIG. 2 the plastic sheet 15 is coated with a layer 17 of a material which has high coefficient of friction. In use, the pad 11 having a structure such as shown in FIG. 2 is placed upon an article (not shown) such that the layer 17 is in contact with the surface of the article or the covering thereon. Therefore, when the patient moves about, there is little or no tendency for the underpad to slip or slide out of position due to the high coefficient of friction of the layer 17.

Figure 3:
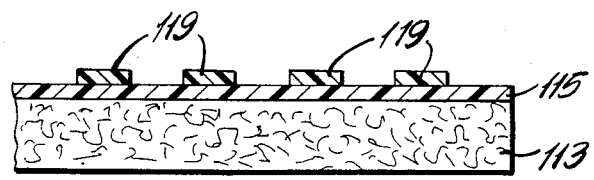
FIG. 3 is a view similar to FIG. 2 showing a different embodiment of the invention.

In the embodiment shown in FIG. 2, the plastic sheet 15 is completely coated with the wax on its entire surface. It is not necessary, however, that the entire plastic surface be coated with the wax in order to realize the advantages of this invention. Thus, as shown in FIG. 3, the moisture-absorbent layer 113 has a water-impervious layer 115 as in the embodiment illustrated in FIG. 2. However, the wax is applied to the layer 115 in several spaced areas such as 119 which preferably define a geometrically regular pattern of spaced areas of high friction coefficient having rectangular, circular, or some other configuration.

Whether applied as a continuous coating or as a pattern, the thickness of the layer or areas of high friction coefficient is not per se critical. Suffice it to say that the thickness of the applied wax must be sufficient to effectively prevent slipping or sliding of the pad relative to the mattress.

It is evident from the foregoing description that the invention herein finds applications for several other types of articles and that several changes and modifications may be made which are nevertheless within the scope of the present invention and are obvious from the disclosure herein.

What is claimed is:

1. A slip resistant article comprising a layer of moisture-absorbent material, water-impervious layer overlying said moisture-absorbent layer and a layer of a wax having a needle penetration value of from about 5 to about 70 and a melting point of from about 150° F. to about 200° F. on said water-impervious layer.

2. An article as in claim 1 wherein said water-impervious layer is made of plastic.

3. A slip resistant article comprising a layer of moisture-absorbent material, water-impervious layer overlying said moisture-absorbent layer, said water-impervious layer having applied to one surface thereof, at a plurality of spaced areas, a wax having a needle penetration of from about 5 to about 70 and a melting point of from about 150° F. to about 200° F.

4. An article as in claim 3 wherein said water-impervious layer is made of plastic.

* * * * *